(12) United States Patent
Casasanta et al.

(10) Patent No.: US 9,844,378 B2
(45) Date of Patent: Dec. 19, 2017

(54) SURGICAL STAPLING APPARATUS AND METHODS OF ADHERING A SURGICAL BUTTRESS THERETO

(71) Applicant: Covidien LP, Mansfield, MA (US)

(72) Inventors: Thomas Casasanta, Kensington, CT (US); Kenneth Whitfield, North Haven, CT (US); Richard Simpson, Hamden, CT (US)

(73) Assignee: Covidien LP, Mansfield, MA (US)

( * ) Notice: Subject to any disclaimer, the term of this patent is extended or adjusted under 35 U.S.C. 154(b) by 699 days.

(21) Appl. No.: 14/264,269

(22) Filed: Apr. 29, 2014

(65) Prior Publication Data

US 2015/0305743 A1 Oct. 29, 2015

(51) Int. Cl.
*A61B 17/068* (2006.01)
*A61B 17/10* (2006.01)
*A61B 17/072* (2006.01)
*A61B 17/00* (2006.01)

(52) U.S. Cl.
CPC .......... *A61B 17/105* (2013.01); *A61B 17/068* (2013.01); *A61B 17/07292* (2013.01); *A61B 2017/0053* (2013.01); *A61B 2017/00884* (2013.01); *A61B 2017/00893* (2013.01); *A61B 2017/0688* (2013.01)

(58) Field of Classification Search
CPC ........ A61B 17/07292; A61B 17/07207; A61B 2017/07271
USPC ....................................... 227/175.1; 606/151
See application file for complete search history.

(56) References Cited

U.S. PATENT DOCUMENTS

| 3,054,406 A | 9/1962 | Usher |
| 3,079,606 A | 3/1963 | Bobrov et al. |
| 3,124,136 A | 3/1964 | Usher |

(Continued)

FOREIGN PATENT DOCUMENTS

| CN | 101310680 A | 11/2008 |
| CN | 101332110 A | 12/2008 |

(Continued)

OTHER PUBLICATIONS

European Search Report corresponding to EP 05 02 2585.3, completed Jan. 25, 2006 and dated Feb. 3, 2006; (4 pp).

(Continued)

*Primary Examiner* — Michelle Lopez (57) ABSTRACT

A surgical stapling apparatus includes a tool assembly, at least one surgical buttress, and a resilient, porous material. The tool assembly includes a cartridge assembly and an anvil assembly pivotably coupled to the cartridge assembly. The cartridge assembly includes a first tissue facing surface defining staple retaining slots. The anvil assembly includes a second tissue facing surface defining staple pockets for forming staples expelled from the staple retaining slots of the cartridge assembly. The at least one surgical buttress is releasably disposed on at least one of the first and second tissue facing surfaces. The resilient, porous material is releasably disposable between the first and second tissue facing surfaces and in contact with the at least one surgical buttress. The resilient, porous material is configured to expel a liquid therefrom upon compression thereof by an approximation of the cartridge assembly and the anvil assembly.

22 Claims, 6 Drawing Sheets

(56) References Cited

U.S. PATENT DOCUMENTS

| | | |
|---|---|---|
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,498,796 A | 2/1985 | Gordon et al. |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B2 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |

(56) References Cited

U.S. PATENT DOCUMENTS

| | | |
|---|---|---|
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,210,810 B1 | 5/2007 | Iversen et |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,823,595 B2 | 11/2010 | Takechi |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 * | 11/2011 | Prommersberger  A61B 17/07207 227/175.1 |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 * | 3/2013 | Shelton, IV ........... A61B 90/92 227/176.1 |
| 8,393,517 B2 | 3/2013 | Milo |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,814,888 B2 | 8/2014 | Sgro |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |

(56) References Cited

U.S. PATENT DOCUMENTS

| | | |
|---|---|---|
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman et al. |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2006/0004407 A1 | 1/2006 | Hiles et al. |
| 2006/0008505 A1 | 1/2006 | Brandon |
| 2006/0025816 A1 | 2/2006 | Shelton |
| 2006/0085030 A1 | 4/2006 | Bettuchi et al. |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |

(56) References Cited

U.S. PATENT DOCUMENTS

| | | |
|---|---|---|
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089220 A1 | 4/2011 | Ingmanson et al. |
| 2011/0089375 A1 | 4/2011 | Chan et al. |
| 2011/0278346 A1 | 11/2011 | Hull et al. |
| 2011/0278347 A1 | 11/2011 | Olson et al. |
| 2011/0293690 A1 | 12/2011 | Griffin et al. |
| 2012/0083723 A1 | 4/2012 | Vitaris et al. |
| 2012/0156289 A1 | 6/2012 | Blaskovich et al. |
| 2012/0187179 A1 | 7/2012 | Gleiman |
| 2012/0197272 A1 | 8/2012 | Oray et al. |
| 2012/0273547 A1 | 11/2012 | Hodgkinson et al. |
| 2013/0037596 A1 | 2/2013 | Bear et al. |
| 2013/0062391 A1 | 3/2013 | Boudreaux et al. |
| 2013/0105548 A1 | 5/2013 | Hodgkinson et al. |
| 2013/0105553 A1 | 5/2013 | (Tarinelli) Racenet et al. |
| 2013/0112731 A1 | 5/2013 | Hodgkinson |
| 2013/0112732 A1 | 5/2013 | Aranyi et al. |
| 2013/0112733 A1 | 5/2013 | Aranyi et al. |
| 2013/0123816 A1 | 5/2013 | Hodgkinson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |

FOREIGN PATENT DOCUMENTS

| | | |
|---|---|---|
| DE | 1602563 U | 3/1950 |
| DE | 19924311 A1 | 11/2000 |
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 A1 | 8/2009 |
| EP | 2 090 244 A2 | 8/2009 |
| EP | 2 090 252 A2 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 258 282 A2 | 12/2010 |
| EP | 2 292 276 A2 | 3/2011 |
| EP | 2 311 386 A2 | 4/2011 |
| EP | 2 462 880 A2 | 6/2012 |
| EP | 2 497 431 A1 | 9/2012 |
| EP | 2 517 637 A1 | 10/2012 |
| EP | 2543339 A1 | 1/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 98/38923 A1 | 9/1998 |
| WO | 99/45849 A1 | 9/1999 |
| WO | 03/088845 A2 | 10/2003 |
| WO | 03082126 A1 | 10/2003 |
| WO | 03/094743 A1 | 11/2003 |

(56) References Cited

FOREIGN PATENT DOCUMENTS

| WO | 03/105698 A2 | 12/2003 |
|---|---|---|
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |
| WO | 2014004209 A2 | 1/2014 |

OTHER PUBLICATIONS

European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 10 25 1437.9, completed Nov. 22, 2010 and dated Dec. 16, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 11 18 8309.6, completed Dec. 15, 2011 and dated Jan. 12, 2012; (3 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013l; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
European Extended Search Report dated Sep. 28, 2015, corresponding to European Applicaiton No. 14199670.2; 8 pages.
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.

(56) References Cited

OTHER PUBLICATIONS

Chinese Office Action corresponding to counterpart Int'l Appln No. CN 201210129787.2 dated Aug. 24, 2015.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Chinese First Office Action corresponding to counterpart Int'l Appln. No. CN 2013107068710 dated Dec. 16, 2016.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. 2013103036903 dated Feb. 23, 2017.
Japanese Office Action corresponding to counterpart Int'l Appln. No. 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).

* cited by examiner

SURGICAL STAPLING APPARATUS AND METHODS OF ADHERING A SURGICAL BUTTRESS THERETO

BACKGROUND

Technical Field

The present disclosure relates to a surgical apparatus having a buttress material incorporated therewith. More particularly, the present disclosure relates to a surgical stapling apparatus including a detachable surgical buttress and a resilient, porous material releasably disposable with the surgical buttress that acts to facilitate adherence of the surgical buttress to tissue facing surfaces of the surgical stapling apparatus.

Background of Related Art

Surgical devices for grasping or clamping tissue between opposing jaw structure and then joining tissue by surgical fasteners are well known in the art. In some instruments, a knife is provided to cut the tissue which has been joined by the fasteners. The fasteners are typically in the form of surgical staples but two-part polymeric fasteners can also be utilized.

Instruments for this purpose can include two elongated jaw members which are respectively used to capture or clamp tissue. In certain surgical staplers, one of the jaw members carries a staple cartridge which houses a plurality of staples arranged in at least two lateral rows while the other jaw member has an anvil that defines a surface for forming the staple legs as the staples are driven from the staple cartridge. The stapling operation is effected by cam members that travel longitudinally through the staple cartridge, with the cam members acting upon staple pushers to sequentially eject the staples from the staple cartridge.

Each of the instruments described above are designed for use in surgical procedures in which surgeons have direct manual access to the operative site. However, in minimally invasive procedures, such as, for example, endoscopic or laparoscopic procedures, surgery is performed through a small incision or through a narrow cannula inserted through small entrance wounds in the skin. In order to address the specific needs of minimally invasive surgical procedures, surgical stapling devices have been developed and are disclosed in, for example, U.S. Pat. No. 5,332,142 (Robinson, et al.); and U.S. Pat. No. 6,241,139 (Milliman et al.), the entire contents of each of which are incorporated by reference herein. These instruments include a surgical stapling apparatus and a loading unit. Typically, the loading unit is attached to the apparatus immediately prior to surgery. After use, the loading unit can be removed from the apparatus and a new loading unit can be fastened to the apparatus to perform additional stapling and/or cutting operations. These instruments have provided significant clinical benefits. Nonetheless, improvements to these instruments are still desirable.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or "buttress" material, between the staple and the underlying tissue. In this method, a layer of buttress material is placed against the tissue and the tissue is stapled in conventional manner. In another method, the buttress material is positioned on the stapling instrument itself prior to stapling the tissue. An example of this is disclosed in U.S. Pat. No. 5,542,594 to McKean et al., the entire contents of which is incorporated by reference herein. In McKean et al., a tube of buttress material is slipped over the jaw of the stapler. The stapler is then actuated to staple the subject tissue and secure the buttress material between the tissue and staple line to reinforce the tissue and staple line.

Buttress materials which are either pre-loaded or are an after-market add-on, for minimally invasive or open mechanical surgical stapling apparatus, may shift in position relative to a stapler reload cartridge assembly and anvil assembly to which they are attached during grasping and manipulation of tissue by the surgical stapling apparatus. If the shifting of the buttress material is pronounced and is not corrected by the surgeon before firing the surgical stapling apparatus, then staples may form outside the perimeter or width of the buttress material thereby reducing the benefits of having the entire staple line reinforced by the buttress material.

SUMMARY

In accordance with the present disclosure, a surgical stapling apparatus is provided. The surgical stapling apparatus includes a tool assembly, a surgical buttress and a resilient, porous material. The tool assembly includes a cartridge assembly and an anvil assembly pivotably coupled to the cartridge assembly. The cartridge assembly includes a first tissue facing surface defining staple retaining slots. The anvil assembly includes a second tissue facing surface defining staple pockets for forming staples expelled from the staple retaining slots of the cartridge assembly. The surgical buttress is releasably disposed on at least one of the first and second tissue facing surfaces. The resilient, porous material is releasably disposable between the first and second tissue facing surfaces and in contact with the surgical buttress. The resilient, porous material is configured to expel a liquid therefrom upon compression thereof by an approximation of the cartridge assembly and the anvil assembly.

In embodiments, the resilient, porous material may include a sponge. The sponge may have an oblong shape and may have a first end and a second end. The sponge may taper from the first end to the second end.

In embodiments, the resilient, porous material may have a length equal to a length of the surgical buttress and a width equal to a width of the surgical buttress. The resilient, porous material may be sized and dimensioned to occupy a space defined between the first and second tissue facing surfaces. The resilient, porous material may have a top surface and bottom surface. The top surface may be in abutting engagement with the second tissue facing surface and the bottom surface may be in abutting engagement with the surgical buttress. It is contemplated that the resilient, porous material may include a water soluble adhesive.

In embodiments, the cartridge assembly and the anvil assembly may be selectively movable relative to one another from a first, spaced apart position to a second, approximated position. In the second, approximated position, the cartridge assembly and the anvil assembly may cooperate to grasp tissue therebetween.

In embodiments, the surgical buttress may be secured to at least one of the anvil assembly and the cartridge assembly by at least one anchor.

In accordance with the present disclosure, a surgical stapling system is provided. The system includes a tool assembly, a surgical buttress, and a resilient, porous material. The tool assembly includes a cartridge assembly and an anvil assembly pivotably coupled to the cartridge assembly. The cartridge assembly includes a first tissue facing surface defining staple retaining slots. The anvil assembly includes a second tissue facing surface defining staple pockets for forming staples expelled from the staple retaining slots of the cartridge assembly. The surgical buttress is releasably disposed on at least one of the first and second tissue facing surfaces. The resilient, porous material is configured to be releasably disposed between the first and second tissue facing surfaces and in contact with the surgical buttress. The resilient, porous material is configured to expel a liquid therefrom upon compression thereof by an approximation of the cartridge assembly and the anvil assembly.

In embodiments, the resilient, porous material may have a length equal to a length of the surgical buttress and a width equal to a width of the surgical buttress.

In accordance with the present disclosure, a method of preparing a surgical stapling apparatus is provided. The method includes providing a tool assembly including a cartridge assembly and an anvil assembly pivotably couple to the cartridge assembly. The cartridge assembly and the anvil assembly each have a tissue facing surface. The method further includes providing at least one surgical buttress releasably secured to the tissue facing surface of at least one of the anvil assembly and the cartridge assembly; disposing a resilient, porous material between the tissue facing surfaces of the cartridge assembly and the anvil assembly such that the resilient, porous material is in abutting engagement with the at least one surgical buttress; wetting the resilient, porous material with a liquid; and approximating the cartridge assembly and the anvil assembly to compress the resilient, porous material therebetween such that the liquid exits the resilient, porous material and contacts the surgical buttress.

In embodiments, the resilient, porous material may have a length equal to a length of the surgical buttress and a width equal to a width of the surgical buttress. The resilient, porous material may be sized and dimensioned to occupy a space defined between the tissue facing surfaces of the cartridge assembly and the anvil assembly. The resilient, porous material may have a top surface and a bottom surface. The top surface may be in abutting engagement with the tissue facing surface of the anvil assembly and the bottom surface may be in abutting engagement with the surgical buttress.

In embodiments, the wetting of the resilient, porous material with a liquid may include inserting the resilient, porous material in a saline solution prior to approximating the cartridge assembly and the anvil assembly.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein.

DETAILED DESCRIPTION OF EMBODIMENTS

Embodiments of the presently disclosed surgical stapling apparatus will now be described in detail with reference to the drawings, in which like reference numerals designate identical or corresponding elements in each of the several views.

In the drawings and in the description that follows, the term "proximal", as is traditional, will refer to the end of the surgical stapling apparatus which is closest to the operator, while the term "distal" will refer to the end of the surgical stapling apparatus which is farthest from the operator.

It should be understood that a variety of surgical stapling apparatus may be utilized with a surgical buttress of the present disclosure. For example, linear stapler configurations may be utilized, such as, for example those including Endo GIA™ Reinforced Reloads and staplers with Tri-Staple™ technology, available through Covidien, and transverse anastomosis staplers, also available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated by reference herein); laparoscopic staplers (see, e.g., commonly owned U.S. Pat. Nos. 6,330,965 and 6,241,139, each entitled "Surgical Stapling Apparatus," the entire contents of each of which are incorporated herein by this reference); and transverse anastomosis staplers (see, e.g., commonly owned U.S. Pat. No. 5,964,394 entitled "Surgical Fastener Applying Apparatus", the entire contents of which are incorporated herein by this reference).

Figure 1:
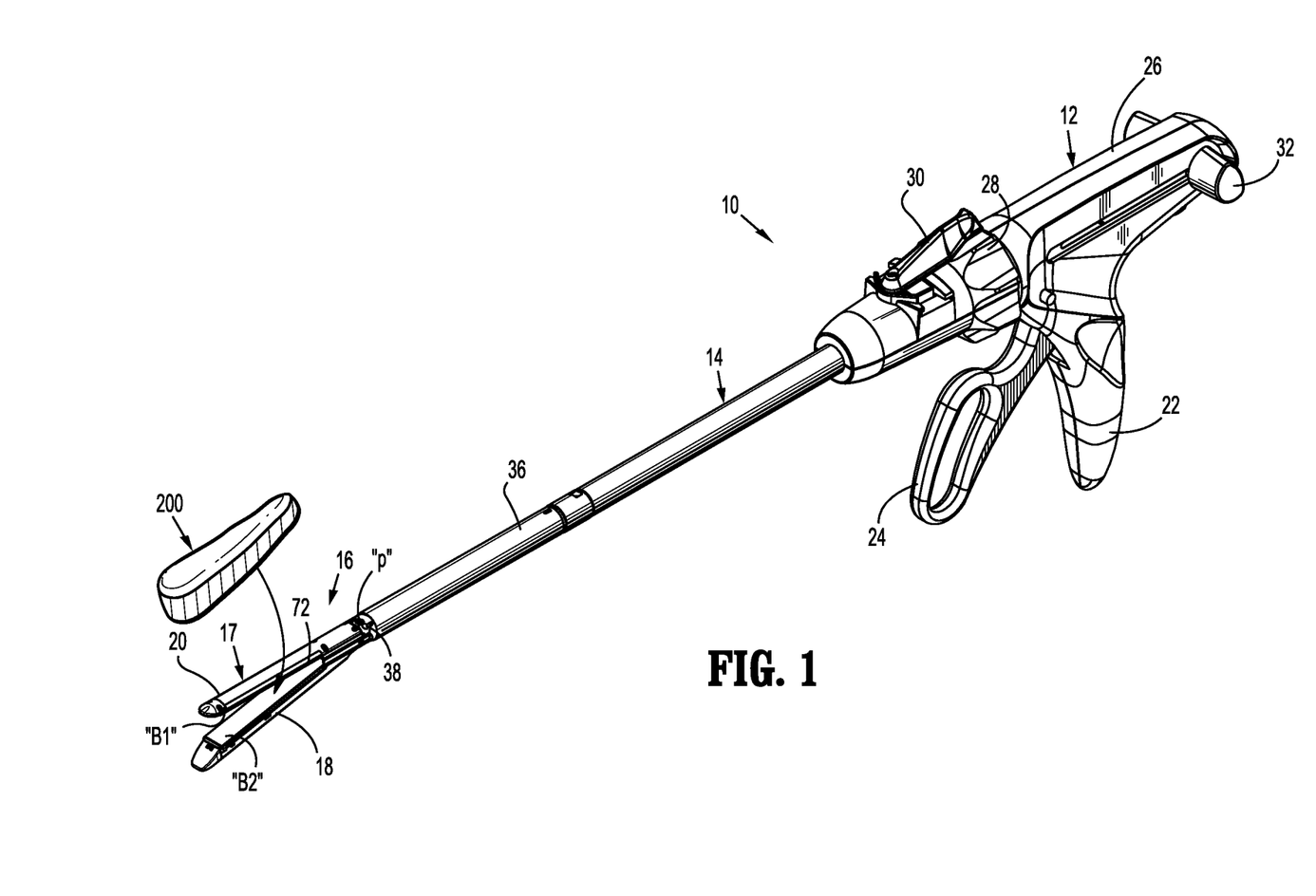
FIG. 1 is a perspective view of a surgical stapling apparatus according to an embodiment of the present disclosure.

FIG. 1 shows a surgical apparatus, e.g., a surgical stapling apparatus, generally referred to as 10 including a loading unit 16, surgical buttresses "B1," "B2" attached thereto, and a resilient, porous material, such as, for example, a sponge, which is generally referred to as 200, disposable therewith. Sponge 200 is used to wet surgical buttresses "B1," "B2" to facilitate an adherence of surgical buttresses "B1," "B2" to surgical fastening apparatus 10. In the interest of brevity, this disclosure will focus primarily on loading unit 16, surgical buttresses "B1," "B2", and sponge 200 of the surgical stapling apparatus 10. A detailed discussion of the remaining components and method of use of surgical stapling apparatus 10 is disclosed in U.S. Pat. No. 6,241,139, the disclosure of which has already been incorporated by reference herein.

Surgical stapling apparatus 10 can be an endoscopic apparatus and includes a handle assembly 12 and an elongated body 14 extending from handle assembly 12. A loading unit 16, which includes a tool assembly 17, is releasably secured to the distal end of elongated body 14. Furthermore, the present disclosure contemplates surgical stapling apparatus that have a replaceable cartridge that is received in the end effector of the apparatus (the end effector may be removable and replaceable or form an integral part of the handle and elongated body).

Handle assembly 12 includes a stationary handle member 22, a movable handle member 24, and a barrel portion 26. A rotatable member 28 is mounted on the forward end of barrel portion 26 to facilitate rotation of elongated body 14 and attached loading unit 16 with respect to handle assembly 12. An articulation lever 30 is also mounted on the forward end of barrel portion 26 adjacent rotatable member 28 to facilitate articulation of tool assembly 17. Preferably, a pair of knobs 32 is movably positioned along barrel portion 26. Knobs 32 are advanced distally to approximate or close tool assembly 17, and retracted proximally to unapproximate or open tool assembly 17.

As shown herein, loading unit 16 (FIG. 2) is configured to apply six (6) linear rows of staples, in loading units measuring from about 30 mm to about 60 mm in length. Loading units for applying any number of rows of staples, having staple pockets arranged in various patterns and/or loading units and end effectors having any other lengths, e.g., 45 mm, are also envisioned.

Figure 2:
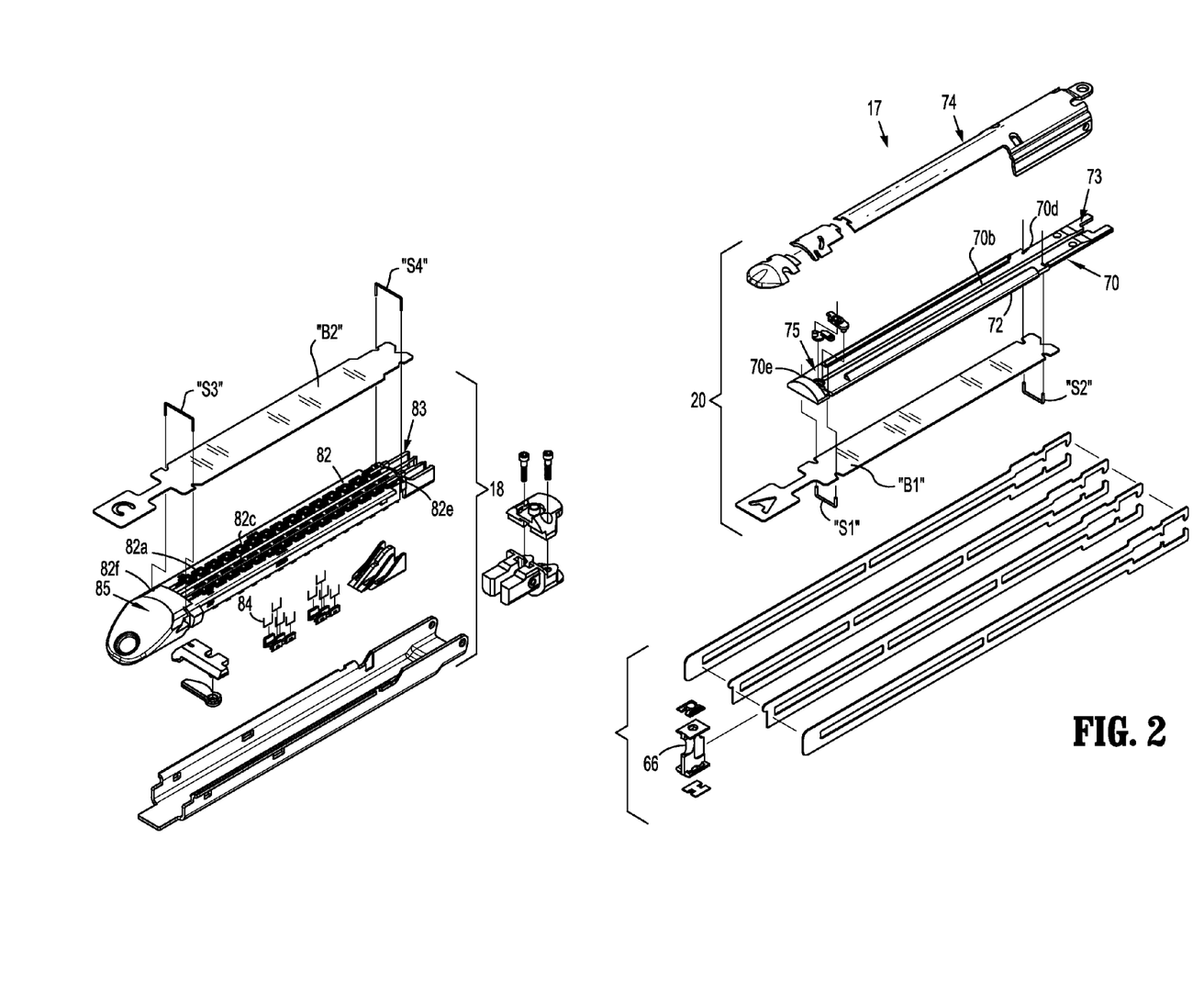
FIG. 2 is a top, perspective view, with parts separated, of a distal end of a loading unit of the surgical stapling apparatus shown in FIG. 1.

Loading unit 16 is desirably selectively removably coupleable to elongated body 14. Loading unit 16 includes a housing portion 36 having a proximal end adapted to releasably engage the distal end of elongated body 14. A mounting assembly 38 is pivotally secured at "P" to the distal end of housing portion 36, and is configured to receive the proximal end of tool assembly 17 such that pivotal movement of tool assembly 17 about an axis at "P", perpendicular to the longitudinal axis of housing portion 36, effects articulation of tool assembly 17.

As mentioned above, loading unit 16 includes a tool assembly 17. Tool assembly 17 includes a cartridge assembly 18 housing a plurality of surgical fasteners or staples 84 (see FIG. 2) and an anvil assembly 20 secured in juxtaposed relation relative to cartridge assembly 18. Anvil assembly 20 and cartridge assembly 18 are selectively moveable, e.g., pivotable, relative to one another from a first, spaced apart position, to a second, approximated position to close tool assembly 17.

Reference may be made to U.S. Pat. No. 7,819,896, filed on Aug. 31, 2009, entitled "TOOL ASSEMBLY FOR A SURGICAL STAPLING DEVICE", the disclosure of which is hereby incorporated by reference herein, for an exemplary discussion of the construction and operation of tool assembly 17, as illustrated in FIG. 2.

With continued reference to FIG. 2, anvil assembly 20 includes an anvil plate 70 having a tissue facing surface 72. A plurality of staple deforming pockets/cavities (not shown) is defined in tissue facing surface 72. Anvil assembly 20 further includes a cover plate 74 secured to a top surface of anvil plate 70, opposite tissue facing surface 72. Anvil plate 70 defines a proximal pair of recesses 70d formed near a proximal end 73 of anvil plate 70 and disposed, one each, on opposed sides of a longitudinal slot 70b. Anvil plate 70 defines a distal pair of recesses 70e formed near a distal end 75 of anvil plate 70 and disposed, one each, on opposed sides of longitudinal slot 70b.

Figure 3A:
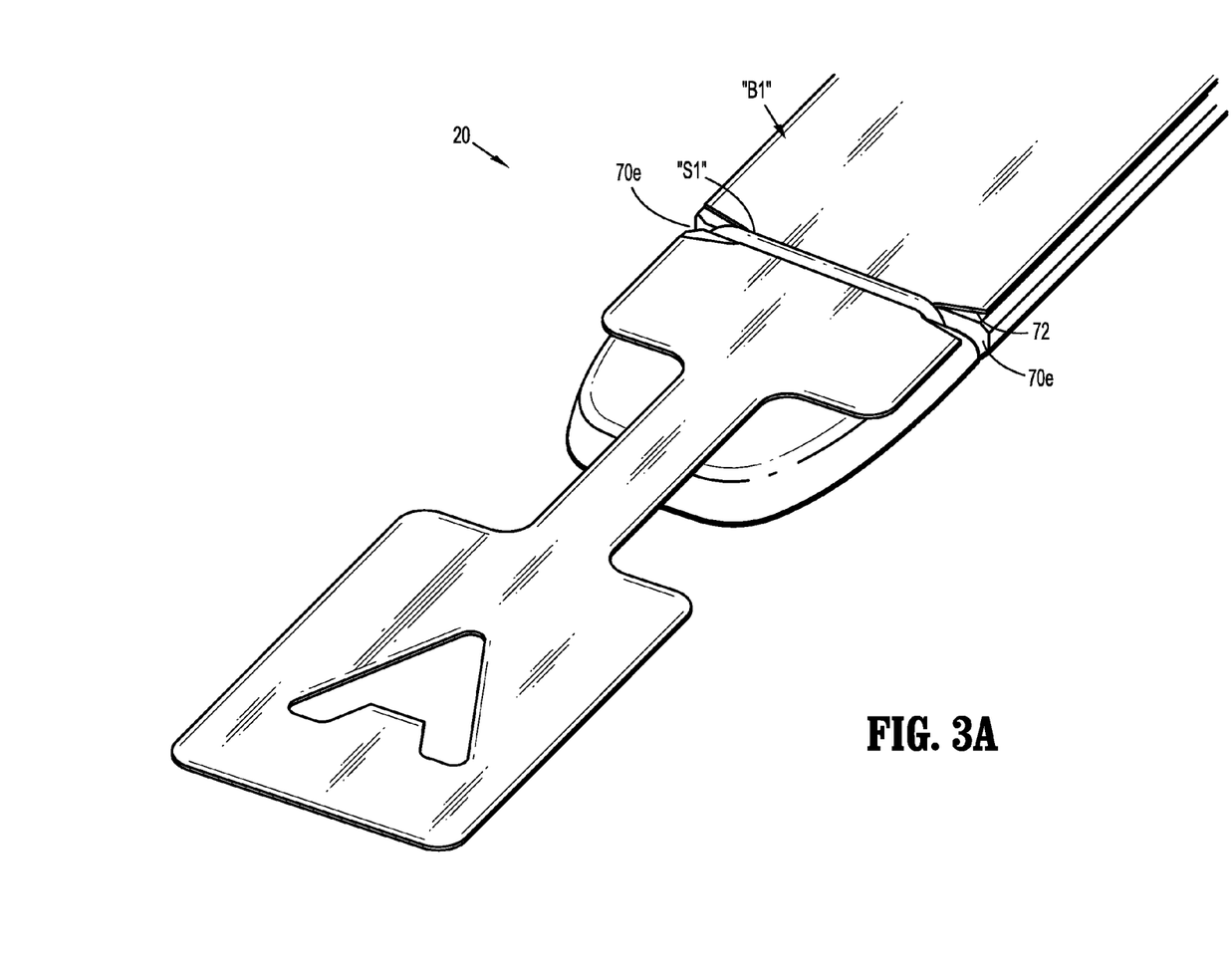
FIG. 3A is an enlarged perspective view of a distal end of an anvil assembly of the loading unit shown in FIG. 2 illustrating a surgical anvil buttress operatively secured to a tissue facing surface thereof.

As seen in FIGS. 2 and 3A, anvil assembly 20 further includes a surgical anvil buttress "B1", pledget or the like operatively secured to a lower surface or tissue facing surface 72 of anvil plate 70, by anchors "S1," "S2" to overlie at least some of the anvil pockets and/or at least a portion of a length of longitudinal slot 70b. In particular, an anchor "S2" is cinched around a proximal portion of surgical anvil buttress "B1" and each of the proximal pair of recesses 70d and an anchor "S1" is cinched around a distal portion of the surgical anvil buttress "B1" and each of the distal pair of recesses 70e. The present application contemplates that the buttress can be attached by other means, such as for example, by use of an adhesive.

Surgical anvil buttress "B1" further includes a tongue or tab extending from a distal edge thereof to facilitate with the attachment of surgical anvil buttress "B1" to anvil assembly 20 during the assembly process. It is contemplated that the tongue is removed from surgical anvil buttress "B1" following securement of surgical anvil buttress "B1" to anvil assembly 20 and prior to packaging or shipment. In some embodiments, surgical anvil buttress "B1" may be removably secured to tissue facing surface 72 of anvil plate 70 via various fastening engagements, such as, for example, adhesives, sutures, and/or frictional engagement.

In operation, with surgical anvil buttress "B1" secured against tissue facing surface 72 of anvil plate 70. During firing of surgical stapling apparatus 10, a knife blade 66 (FIG. 2) may slice through a central section of the proximal suture "S2", thereby freeing the proximal end of the surgical anvil buttress "B1" from anvil assembly 20. During use, as the firing stroke of surgical stapling apparatus 10 is nearing completion, a release mechanism (not shown) releases distal suture "S1" and the surgical anvil buttress "B1" is free to separate from tissue facing surface 72 of anvil plate 70. The release mechanism may include a separate knife for slicing the anchor or anchors, or may include a bar or other member for simply pushing the anchor from a constricting slot. In embodiments, after surgical buttress "B1" is stapled and secured with tissue, the opening of tool assembly 17 provides a sufficient amount of force to separate surgical buttress "B1" from tissue facing surface 72 of anvil plate 70.

Figure 3B:
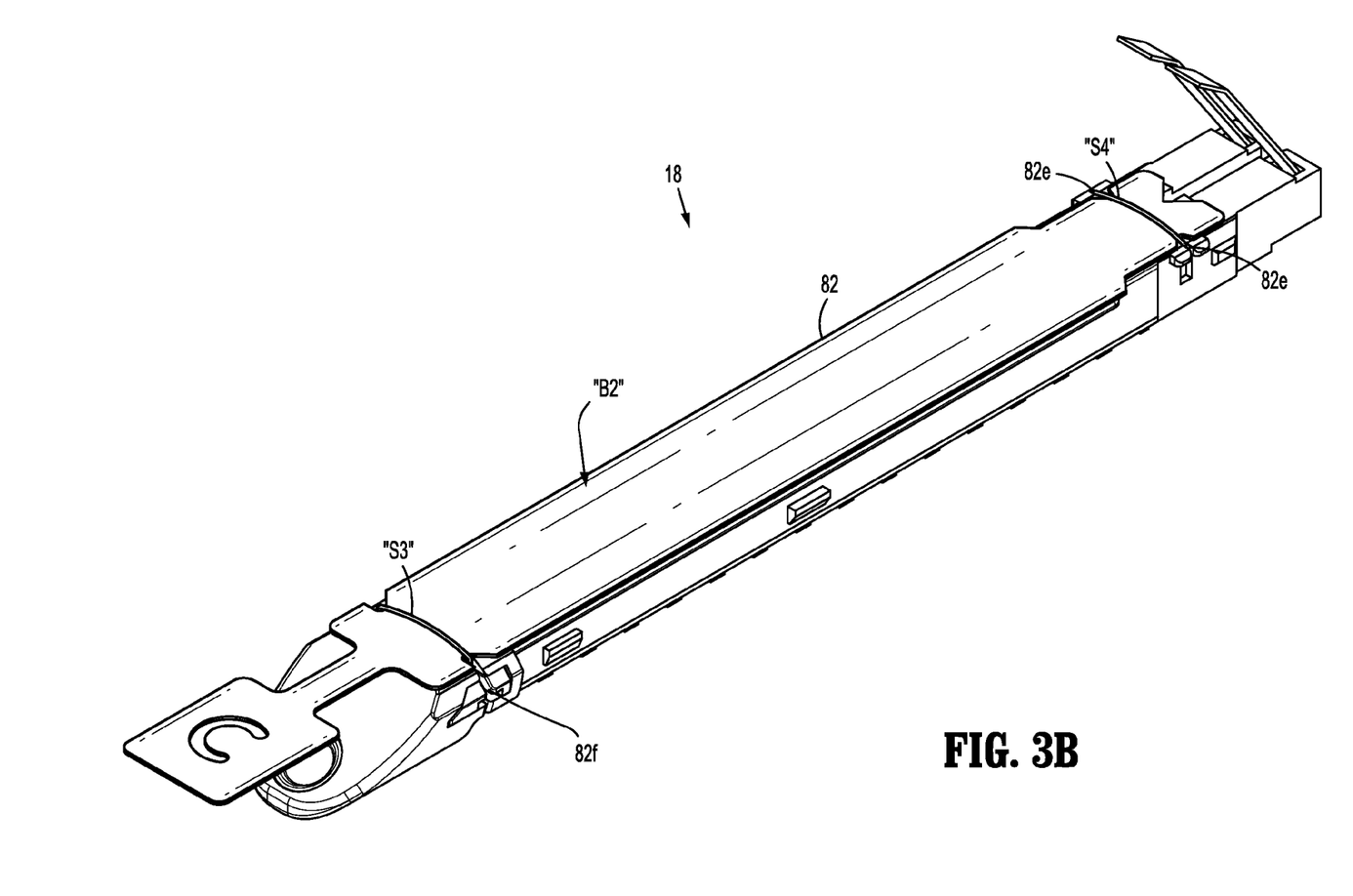
FIG. 3B is an enlarged perspective view of a cartridge assembly of the loading unit shown in FIG. 2 illustrating a surgical cartridge buttress secured to a tissue facing surface thereof.

As seen in FIGS. 1, 2, and 3B, cartridge assembly 18 includes a tissue facing surface 82 defining retention slots 82a formed therein for receiving a plurality of fasteners 84 and pushers 86. Cartridge assembly 18 defines a proximal pair of recesses 82e formed near a proximal end 83 thereof and disposed, one each, on opposed sides of a longitudinal slot 82c. Staple cartridge assembly 18 further defines a distal pair of recesses 82f formed near a distal end 85 thereof and disposed, one each, on opposed sides of longitudinal slot 82c. In one embodiment, at least one of the recesses of each of the proximal pair of recesses 82e and the distal pair of recesses 82f is preferably non-circular and constricting or otherwise arranged so as to frictionally engage and/or pinch anchors "S3," "S4."

As seen in FIGS. 2 and 3B, cartridge assembly 18 further includes a surgical cartridge buttress "B2", pledget or the like operatively secured to an upper surface or tissue facing surface 82 of staple cartridge assembly 18, by anchors "S3" and "S4", to overlie at least some of staple pockets 82a and/or at least a portion of a length of longitudinal slot 82c. In particular, an anchor "S4" is cinched around a proximal portion of surgical cartridge buttress "B2" and each of the proximal pair of recesses 82e, and an anchor "S3" is cinched around a distal portion of the surgical cartridge buttress "B2" and each of the distal pair of recesses 82f. In some embodiments, surgical cartridge buttress "B2" may be removably secured to tissue facing surface 82 of cartridge assembly 18 via various fastening engagements, such as, for example, adhesives, sutures, and/or frictional engagement. In some embodiments, only one of tissue facing surfaces 72, 82 has a surgical buttress attached thereto.

Exemplary surgical buttresses for use with the surgical stapling devices disclosed herein are shown and described in commonly assigned U.S. Pat. Nos. 5,542,594; 5,908,427; 5,964,774; and 6,045,560, and commonly assigned U.S. application Ser. No. 12/579,605, filed on Oct. 15, 2009 (now U.S. Patent Publication No. 2010/0092710, now U.S. Pat. No. 8,157,151), commonly assigned U.S. application Ser. No. 11/241,267, filed on Sep. 30, 2005 (U.S. Patent Publication No. 2006/0085034, now U.S. Pat. No. 7,938,307), and U.S. application Ser. No. 11/248,846, filed on Oct. 12, 2005 (U.S. Patent Publication No. 2006/0135992, now U.S. Pat. No. 7,823,592), the entire contents of each of which is incorporated herein by reference. The buttress may also be made according to methods and materials disclosed in U.S. Publication Nos. 2013/0123816 and/or 2013/0112731, the disclosure of which are hereby incorporated by reference herein in their entirety.

In accordance with the present disclosure, and either in place of or in addition to the methods and systems disclosed above for attaching surgical buttresses "B1, B2" to the tissue facing/contacting surface 72 of anvil assembly 20 and/or tissue facing/contacting surface 82 of cartridge assembly 18 of surgical stapling apparatus 10, surgical buttresses "B1, B2" may be further attached to the tissue facing surfaces 72, 82 of surgical stapling apparatus 10 in a number of different ways.

Figure 4:
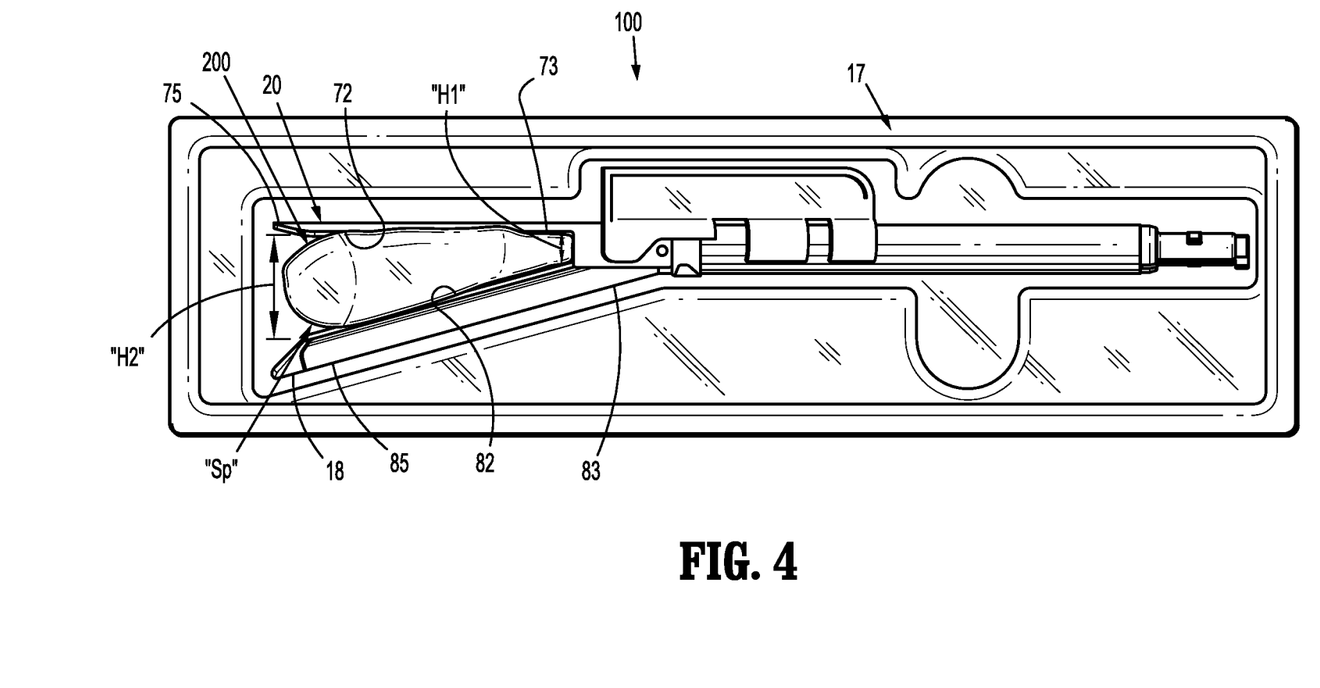
FIG. 4 is a perspective view of a loading unit disposed in a package and including a cartridge assembly and a resilient, porous material according to an embodiment of the present disclosure.
Figure 5A:
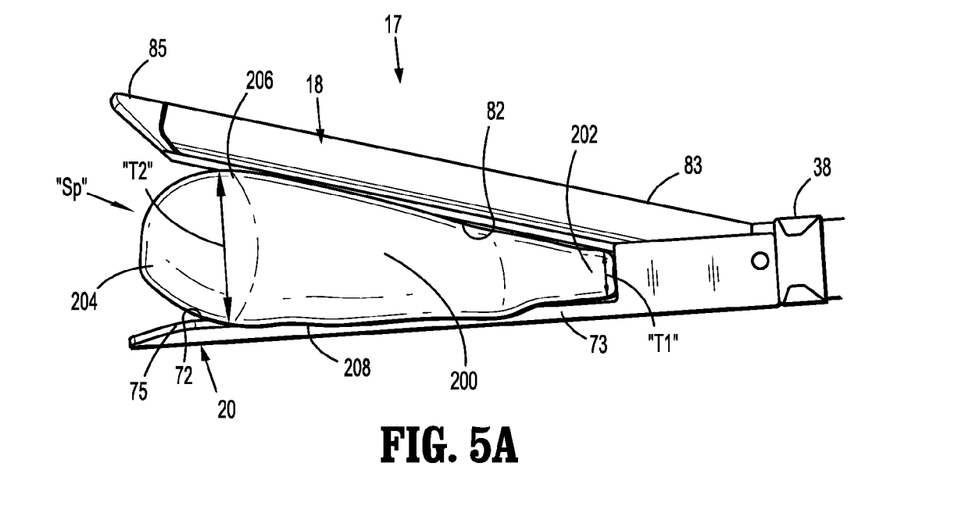
FIG. 5A illustrates the resilient, porous material shown in FIG. 4 in a first, expanded state prior to a closing of the loading unit shown in FIG. 2.
Figure 5B:
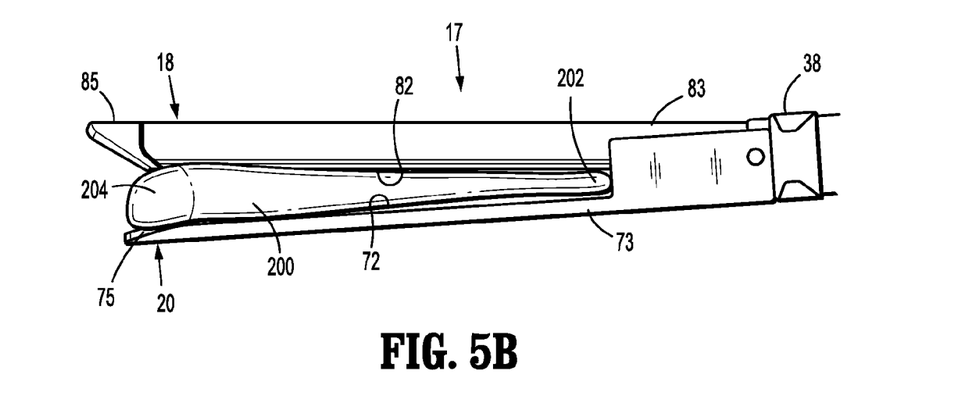
FIG. 5B illustrates the resilient, porous material shown in FIG. 4 in a second, compressed state after a closing of the loading unit shown in FIG. 4.

With reference to FIGS. 4, 5A, and 5B, a sponge 200, which is disposable with tool assembly 17, is shown. Sponge 200 and tool assembly 17 may be provided as a surgical fastener system 100, as shown in FIG. 4. Sponge 200 and tool assembly 17 can be disposed in a bubble packaging sized and dimensioned to accommodate both sponge 200 and tool assembly 17 and maintain sponge 200 and tool assembly 17 in a sterile and compact condition. Sponge 200 is made of a resilient or compressible material that has a porosity configured to readily absorb and retain liquids therein and to expel a liquid therefrom upon compression thereof, as described in detail below.

In embodiments, sponge 200 may be made of various materials, such as, for example, natural, man-made, and/or synthetic materials, or may include synthetic materials manufactured from natural materials, such as synthetic fibers manufactured from natural cellulose. Sponge 200 may be formed from cellulose, cellulose esters such as cellulose acetate and cellulose triacetate, and materials of a cellulosic nature such as cotton or rayon. Sponge 200 may also be formed from polyamides such as nylon, polyolefins such as polyethylene and polypropylene, acrylics, modacrylics, rubber, plastic, thermoplastics, polyvinyl alcohol, polyester, polyurethane, polyether urethane, polyvinyl chloride, vinyl nitrile, silicone, latex, combinations and derivatives thereof, and other absorbent materials within the purview of those skilled in the art. Sponge 200 may also include reticulated, open, and/or closed cell foams.

Sponge 200 is sized and dimensioned to be releasably disposed between tissue facing surfaces 72, 82 of anvil assembly 20 and cartridge assembly 18. Sponge 200 is sized and dimensioned to occupy a substantially V-shaped space "SP" defined between tissue facing surfaces 72, 82 of anvil assembly 20 and cartridge assembly 18 when tool assembly 17 is in the open position, as shown in FIGS. 4 and 5A. When sponge 200 is disposed between tissue facing surfaces 72, 82, sponge 200 abuts surgical buttresses "B1", "B2" to resiliently bias tool assembly 17 toward the open position. It is contemplated that sponge 200 includes straps, belts, hooks, elastic bands or the like (not shown) that can be slipped over cartridge assembly 18 and/or anvil assembly 20 to assist in securing sponge 200 therewith.

Sponge 200 has a first end or proximal end 202 and a second end or distal end 204 and defines a tapered profile therebetween. Sponge 200 has an oblong shape that conforms or corresponds to the shape of space "SP" of tool assembly 17. First end 202 of sponge 200 has a thickness "T1" that is less than a thickness "T2" of second end 204 of sponge 200 such that sponge 200 tapers between first end 202 to second end 204. Thickness "T1" of first end 202 is substantially equal to a height "H1" (FIG. 4) defined between proximal ends 83, 73 of cartridge assembly 18 and anvil assembly 20 when tool assembly 17 is in the open position, as shown in FIGS. 4 and 5A. Second end 204 of sponge 200 has a thickness "T2" substantially equal to a height "H2" (FIG. 4) defined between distal ends 85, 75 of cartridge assembly 18 and anvil assembly 20 when tool assembly 17 is in the open position, as shown in FIGS. 4 and 5A. Sponge 200 has a length substantially equal to a length of surgical buttresses "B1", "B2" and a width substantially equal to a width of surgical buttresses "B1", "B2" such that surface area contact between sponge 200 and surgical buttresses "B1", "B2" is maximized. In this way, sponge 200 has an overall shape corresponding to a shape of space "SP."

Sponge 200 has a top surface 206 and a bottom surface 208 each extending between first and second ends 202, 204. Surfaces 206, 208 may be planar to maximize surface area contact between sponge 200 and surgical buttresses "B1", "B2". In embodiments, longitudinal grooves or channels (not shown) are defined in top and bottom surfaces 206, 208 that are configured to accommodate tissue facing surfaces 72, 82 of anvil assembly 20 and cartridge assembly 18, respectively, such that lateral movement of sponge 200 within space "SP" of tool assembly 17 is resisted and/or prevented. When sponge 200 is disposed within space "SP" of tool assembly 17, top surface 206 is in abutting engagement with surgical buttress "B1" or tissue facing surface 72 of anvil assembly 20 and bottom surface 208 is in abutting engagement with surgical buttress "B2" or tissue facing surface 82 of cartridge assembly 18.

In some embodiments, sponge 200 may be variously shaped and configured, such as, for example, uniform, non-uniform, planar, undulating, arcuate, rectangular, circular, triangular, V-shaped, U-shaped, polygonal and/or variable. In some embodiments, ledges or lips (not shown) extend from distal ends 204 of top and bottom surfaces 206, 208 that are configured to overlap with distal ends 75, 85 of anvil assembly 20 and cartridge assembly 18 to resist and/or prevent sponge 200 from moving distally out from between cartridge assembly 18 and anvil assembly 20.

Sponge 200 can include a water soluble adhesive, for example, a polysaccharide, that when wet will facilitate a releasable retention of surgical buttresses "B1", "B2" with tissue facing surfaces 82, 72 of cartridge assembly 18 and anvil assembly 20. In some embodiments, surgical buttresses "B1," "B2" include a first composition and sponge 200 includes a second composition. Upon wetting and combining the first and second compositions, an adhesive is formed. It is contemplated that sponge 200 may be pre-wetted and encapsulated such that upon approximation of cartridge assembly 18 and anvil assembly 20, the capsule is broken to expose pre-wetted sponge 200.

In operation, loading unit 16 is coupled to elongate body 14 of surgical fastening apparatus 10. With tool assembly 17 in the open or unapproximated position, as shown in FIGS. 4 and 5A, sponge 200 is disposed between tissue facing surfaces 72, 82 such that sponge 200 is in abutting engagement with surgical buttresses "B1", "B2". Sponge 200 is wetted by, for example, inserting tool assembly 17 into a bath of liquid, such as, for example, a saline solution. It is contemplated that tool assembly 17 can be closed and then opened while immersed in the saline solution to facilitate absorption of the saline solution into sponge 200. It is further contemplated that sponge 200 is wetted prior to being positioned between tissue facing surfaces 72, 82. Therefore, the step of wetting sponge 200 may include sponge 200 being pre-wetted. For example, as described above, sponge 200 may be pre-wetted and disposed within a capsule that is configured to break upon a closing of tool assembly 17. In some embodiments, the bath of liquid may include an adhesive.

Handle assembly 12 is actuated to approximate cartridge assembly 18 and anvil assembly 20. The approximation of cartridge assembly 18 and anvil assembly 20 compresses sponge 200 therebetween, as shown in FIG. 5B. Compression of sponge 200 causes the saline solution to exit sponge 200 and contact surgical buttresses "B1", "B2." The clamping pressure or force provided by the closing of tool assembly 17, which is transferred to surgical buttresses "B1", "B2" via sponge 200, causes the saline solution to penetrate and/or impregnate surgical buttresses "B1", "B2." It is envisioned that sponge 200 is sufficiently resiliently biased to its uncompressed or natural state, as shown in FIG. 5A, such that liquid contained therein is forcefully expelled from sponge 200 upon compression thereof.

Tool assembly 17 may be held in the fully approximated position, as shown in FIG. 5B, so that sponge 200 can continue to transfer the saline solution therefrom to surgical buttresses "B1", "B2." Sponge 200 is removed from between tissue facing surfaces 82, 72 of cartridge assembly 18 and anvil assembly 20 such that surgical fastening apparatus 10 can be used in its ordinary manner for stapling tissue.

In accordance with the principles of the present disclosure, sponge 200 effectively drives liquid into and/or onto surgical buttresses "B1", "B2" to at least partially saturate surgical buttresses "B1", "B2" with the liquid. It has been found that surgical buttresses in a wetted condition better adhere to tissue facing surfaces of a cartridge assembly and an anvil assembly compared to dry surgical buttresses. Accordingly, with surgical buttresses "B1", "B2" at least partially saturated with liquid via use of sponge 200, surgical buttresses "B1", "B2" are resisted and/or prevented from shifting or sliding laterally along tissue facing surfaces 72, 82 during use of surgical fastening apparatus 10.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:

1. A surgical stapling apparatus, comprising:
a cartridge assembly including a first tissue facing surface defining staple retaining slots;
an anvil assembly pivotably coupled to the cartridge assembly and including a second tissue facing surface defining staple pockets for forming staples expelled from the staple retaining slots of the cartridge assembly;
at least one surgical buttress releasably disposed on one of the first and second tissue facing surfaces; and
a resilient, porous material releasably disposed between the first and second tissue facing surfaces and in contact with the at least one surgical buttress, the resilient, porous material resiliently biasing the cartridge and anvil assemblies toward a spaced apart position, wherein the resilient, porous material is configured to expel a liquid therefrom upon compression thereof by an approximation of the cartridge assembly and the anvil assembly, the resilient, porous material including a top surface and a bottom surface, a distal portion of each of the top and bottom surfaces being in abutting engagement with a respective distal portion of each of the cartridge and anvil assemblies when the cartridge and anvil assemblies are in the spaced apart position.

2. The surgical stapling apparatus of claim 1, wherein the resilient, porous material is a sponge.

3. The surgical stapling apparatus of claim 2, wherein the sponge has an oblong shape and has a first end and a second end, wherein the sponge tapers from the first end to the second end.

4. The surgical stapling apparatus of claim 1, wherein the resilient, porous material has a length equal to a length of the at least one surgical buttress and a width equal to a width of the at least one surgical buttress.

5. The surgical stapling apparatus of claim 1, wherein the resilient, porous material is sized and dimensioned to occupy a space defined between the first and second tissue facing surfaces when the cartridge and anvil assemblies are in the spaced apart position.

6. The surgical stapling apparatus of claim 1, wherein the bottom surface is in abutting engagement with the at least one surgical buttress when the cartridge and anvil assemblies are in the spaced apart position.

7. The surgical stapling apparatus of claim 1, wherein the cartridge assembly and the anvil assembly are selectively movable relative to one another from the spaced apart position, to an approximated position, wherein the cartridge assembly and the anvil assembly cooperate to grasp tissue therebetween.

8. The surgical stapling apparatus of claim 1, wherein the resilient, porous material includes a water soluble adhesive.

9. The surgical stapling apparatus of claim 1, wherein the at least one surgical buttress is secured to at least one of the anvil assembly and the cartridge assembly by at least one anchor.

10. A surgical stapling system, comprising:
a tool assembly including:
a cartridge assembly including a first tissue facing surface defining staple retaining slots;
an anvil assembly pivotably coupled to the cartridge assembly and including a second tissue facing surface defining staple pockets for forming staples expelled from the staple retaining slots of the cartridge assembly; and
a surgical buttress releasably disposed on the first tissue facing surface of the cartridge assembly; and
a resilient, porous material configured to be releasably disposed between the first and second tissue facing surfaces and on top of and in contact with the surgical buttress, the resilient, porous material resiliently biasing the cartridge and anvil assemblies toward a spaced apart position, wherein the resilient, porous material is configured to expel a liquid therefrom upon compression thereof by an approximation of the cartridge assembly and the anvil assembly.

11. The surgical stapling system of claim 10, wherein the resilient, porous material is a sponge.

12. The surgical stapling system of claim 11, wherein the sponge has an oblong shape and has a first end and a second end, wherein the sponge tapers from the first end to the second end.

13. The surgical stapling system of claim 10, wherein the resilient, porous material has a length equal to a length of the surgical buttress and a width equal to a width of the surgical buttress.

14. The surgical stapling system of claim 10, wherein the resilient, porous material includes a water soluble adhesive.

15. A method of preparing a surgical stapling apparatus, the method comprising:
providing a tool assembly including:
a cartridge assembly having a first tissue facing surface; and
an anvil assembly having a second tissue facing surface;
providing at least one surgical buttress releasably secured to the first or second tissue facing surfaces;
disposing a resilient, porous material between the first and second tissue facing surfaces such that the resilient, porous material is in abutting engagement with the at least one surgical buttress and resiliently biases the cartridge and anvil assemblies toward a spaced apart position, the resilient, porous material including a top surface and a bottom surface, a distal portion of each of the top and bottom surfaces being in abutting engagement with a respective distal portion of each of the cartridge and anvil assemblies when the cartridge and anvil assemblies are in the spaced apart position;
wetting the resilient, porous material with a liquid; and
approximating the cartridge assembly and the anvil assembly from the spaced apart position to an approximated position to compress the resilient, porous material therebetween such that the liquid exits the resilient, porous material and contacts the at least one surgical buttress.

16. The method of claim 15, wherein the resilient, porous material is a sponge.

17. The method of claim 16, wherein the sponge has an oblong shape and has a first end and a second end, wherein the sponge tapers from the first end to the second end.

18. The method of claim 15, wherein the resilient, porous material has a length equal to a length of the at least one surgical buttress and a width equal to a width of the at least one surgical buttress.

19. The method of claim 15, wherein the resilient, porous material is sized and dimensioned to occupy a space defined between the first and second tissue facing surfaces when the cartridge and anvil assemblies are in the spaced apart position.

20. The method of claim 15, wherein the bottom surface is in abutting engagement with the at least one surgical buttress.

21. The method of claim 15, wherein the wetting of the resilient, porous material includes inserting the resilient, porous material in a saline solution prior to approximating the cartridge assembly and the anvil assembly.

22. The method of claim 15, wherein the resilient porous material includes a water soluble adhesive.

* * * * *